US011129966B2

(12) United States Patent
Anzalone et al.

(10) Patent No.: US 11,129,966 B2
(45) Date of Patent: Sep. 28, 2021

(54) SYSTEMS AND METHODS FOR INTRAVENOUS CATHETER STABILIZATION AND MONITORING

(71) Applicant: THE CHILDREN'S HOSPITAL OF PHILADELPHIA, Philadelphia, PA (US)

(72) Inventors: Jacqueline Anzalone, Philadelphia, PA (US); Michele Russen Davey, Ardmore, PA (US); Cheryl Gebeline-Myers, Wayne, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 20 days.

(21) Appl. No.: 16/300,071

(22) PCT Filed: May 15, 2017

(86) PCT No.: PCT/US2017/032602
§ 371 (c)(1),
(2) Date: Nov. 9, 2018

(87) PCT Pub. No.: WO2017/200904
PCT Pub. Date: Nov. 23, 2017

(65) Prior Publication Data
US 2019/0175877 A1 Jun. 13, 2019

Related U.S. Application Data

(60) Provisional application No. 62/337,032, filed on May 16, 2016.

(51) Int. Cl.
*A61M 25/02* (2006.01)
*A61F 15/00* (2006.01)

(52) U.S. Cl.
CPC ............. *A61M 25/02* (2013.01); *A61F 15/00* (2013.01); *A61M 2025/0206* (2013.01); *A61M 2025/026* (2013.01); *A61M 2025/028* (2013.01)

(58) Field of Classification Search
CPC .......... A61M 25/02; A61M 2025/0213; A61M 2025/024; A61M 2025/0246; A61M 2025/0206; A61M 2025/0253; A61M 2025/026; A61M 2025/028; A61M 25/04; A61M 2025/0233; A61M 2025/0266;
(Continued)

(56) References Cited

U.S. PATENT DOCUMENTS 3,782,378 A 1/1974 Page
4,470,410 A * 9/1984 Elliott .................... A61M 5/52
128/877

(Continued)

OTHER PUBLICATIONS

PCT International Search Report and Written Opinion issued in International Application No. PCT/US2017/032602, dated Aug. 10, 2017.

*Primary Examiner* — Amber R Stiles
*Assistant Examiner* — Alexandra Lalonde
(74) *Attorney, Agent, or Firm* — Parker Highlander PLLC

(57) ABSTRACT

Devices and methods for securing a catheter and monitoring a catheter insertion site. Exemplary embodiments can allow monitoring of the site without removal of the device. Exemplary embodiments can also secure a catheter while maintaining patient comfort.

13 Claims, 4 Drawing Sheets

(58) Field of Classification Search
CPC .. A61M 2025/0273; A61M 2025/0286; A61M 2025/0293; A61M 2025/022; A61M 2025/0226; A61F 15/00
See application file for complete search history.

(56) References Cited

U.S. PATENT DOCUMENTS

| | | | |
|---|---|---|---|
| 4,662,873 A * | 5/1987 | Lash | A61M 25/02 128/DIG. 26 |
| 4,917,112 A | 4/1990 | Kalt | |
| 4,930,500 A | 6/1990 | Morgan | |
| 5,018,534 A | 5/1991 | Grant | |
| 5,074,847 A | 12/1991 | Greenwell et al. | |
| 5,112,313 A | 5/1992 | Sallee | |
| 5,116,324 A * | 5/1992 | Brierley | A61M 25/02 128/DIG. 6 |
| 5,167,240 A | 12/1992 | Rozier et al. | |
| D335,926 S | 5/1993 | Rozier et al. | |
| 5,238,010 A | 8/1993 | Grabenkort et al. | |
| 5,336,195 A | 8/1994 | Daneshvar | |
| D359,120 S | 6/1995 | Sallee et al. | |
| 5,449,349 A | 9/1995 | Sallee et al. | |
| 5,456,660 A | 10/1995 | Reich et al. | |
| 5,577,516 A | 11/1996 | Schaeffer | |
| 5,897,519 A | 4/1999 | Shesol et al. | |
| 6,526,981 B1 | 3/2003 | Rozier et al. | |
| 2003/0216663 A1 | 11/2003 | Jersey-Willuhn et al. | |
| 2006/0211994 A1 | 9/2006 | Roman et al. | |
| 2008/0097334 A1 * | 4/2008 | Dikeman | A61M 25/02 604/180 |
| 2010/0081996 A1 | 4/2010 | Fink et al. | |
| 2011/0040258 A1 | 2/2011 | Robison | |
| 2011/0060295 A1 * | 3/2011 | Hen | A61L 15/44 604/290 |
| 2013/0110048 A1 * | 5/2013 | Herzog | A61M 25/02 604/179 |
| 2013/0296793 A1 | 11/2013 | Propp | |
| 2014/0060547 A1 * | 3/2014 | Vallino | A61F 5/3761 128/845 |
| 2014/0276658 A1 * | 9/2014 | Ward | A61M 27/00 604/541 |

* cited by examiner

SYSTEMS AND METHODS FOR INTRAVENOUS CATHETER STABILIZATION AND MONITORING

CROSS-REFERENCE TO RELATED APPLICATIONS

This application is a national phase application under 35 U.S.C. § 371 of International Application Serial No. PCT/US2017/032602, filed May 15, 2017, which claims priority to U.S. Provisional Patent Application Ser. No. 62/337,032, filed May 16, 2016, the entire contents of each disclosure referenced above is incorporated by reference herein.

BACKGROUND INFORMATION

Catheters are an important component in modern medicine, but their application includes numerous challenges for successful implementation. One significant concern is the risk of intentional and/or unintentional dislodgment of the catheter. Catheter dislodgment is associated with unwanted complications, including for example, an increased risk of infiltration (e.g. unwanted leakage of intravenous fluids into surrounding tissue) and inflammation.

Catheters include many different configurations, including a peripheral intravenous (PIV) catheter, also known as a peripheral venous line or peripheral venous access catheter. A PIV catheter is a small, flexible tube placed into a peripheral vein in order to administer medication or fluids. The catheter is typically introduced into a vein by a needle (similar to blood drawing), which is subsequently removed while the small tube of the cannula remains in place. The catheter is typically then be fixed by taping it to the patient's skin or other similar procedures.

A peripheral intravenous catheter is usually placed in a vein on the hand or arm, and in the foot or leg of some neonates and infants. It can be distinguished from a central venous catheter, which is inserted in a central vein (usually in the internal jugular vein of the neck or the subclavian vein of the chest), or an arterial catheter which can be placed in a peripheral as well as a central artery. In children, a local anesthetic gel (such as lidocaine) can be applied to the insertion site to facilitate placement. The peripheral intravenous catheter is the most commonly used vascular access in medicine. It is given to most emergency room and surgical patients, and before some radiological imaging techniques using radio contrast, for example.

Nearly two hundred million peripheral intravenous catheters are used each year in United States hospitals alone [1]. Such devices are the most commonly used invasive device in hospitals [2] and are in use in at least forty-four percent of pediatric inpatients [3]. There are approximately two hundred and nine children's hospitals or care facilities across the United States. Based on 2009 Healthcare Cost and Utilization (HCUP) data, there were over 6.4 million hospital stays for children seventeen years of age and younger accounting for nearly seventeen percent of all hospital stays captured in this dataset [5]. In pediatrics alone, estimates would provide that there are nearly 2.8 million annual pediatric PIVs placed in the United States. PIVs are also widely used in geriatric populations where securement and protection are also of concern. In 2009, there were over nine million hospital admissions in patients age sixty-five years of age and older [6].

Insertion of a venous cannula can be a painful procedure that can lead to anxiety and stress. Use of a vapocoolant immediately before cannulation can reduce pain during the procedure, without increasing the difficulty of cannulation [4]. Although a common procedure, there is a risk of infection, phlebitis, extravasation, infiltration, air embolism, hemorrhage (bleeding) or formation of a hematoma (bruise). Because of the risk of insertion-site infection, the CDC advises in their guideline that the catheter needs to be replaced every 96 hours [5]. Although these catheters should not be left in place longer than necessary, the need to replace these catheters routinely is debated [6]. Expert management has been shown to reduce the complications of peripheral lines [3, 7].

In many patients (including pediatric, geriatric and developmentally-impaired patients) with PIVs, the catheter needs to be protected to prevent dislodgment or injury secondary to patient or incidental manipulation. At the same time, the health care team members, specifically the bedside nurses, need to be able to appropriately access and assess the catheter insertion site. This assessment and monitoring of the insertion site is typically performed on a frequent basis, including for example, hourly.

Existing devices directed to securement of catheters include numerous shortcomings. For example, some devices use plastic protection cups that do not allow for clear visualization or direct palpation of the site. In addition, some devices utilize a hook-and-loop fastener (e.g. Velcro®) securement that does not provide for stabilization of the insertion extremity and creates considerable noise when adjusting. Still other devices allow for direct visualization of the catheter insertion site but do not cover or protect the insertion site.

Other related devices include elastic fabric sleeve and wrap products aimed at securing primarily peripherally inserted central catheter (PICC) lines and central venous catheters. These covering devices include a pocket concept that allows for hiding the caps and extensions while not in use, but do not include a window to allow for easy and direct access, visualization and palpation to the insertion site with minimal interruption to the patients. In addition, such devices do not include a stability device to help support and prevent dislodgement of the catheter from the patient.

Existing devices also include stabilization boards that typically do not allow for direct visualization of the skin under the boards. In addition, existing stabilization boards are not configured to be used in conjunction with catheter securement devices that include panels to allow for direct visualization.

As discussed in further detail below, exemplary embodiments of the present disclosure address shortcomings of existing systems and provide notable benefits in comparison to such systems.

SUMMARY

Exemplary embodiments of the present disclosure comprise systems and methods for securing and monitoring catheters, including peripheral intravenous catheters.

Exemplary embodiments include a central portion with a transparent covered opening providing a more direct visualization of the insertion site and surrounding tissue. Exemplary embodiments may also include a stabilization board that allows for visualization on the opposite side of the extremity. The transparent cover allows the care provider to see the insertion site while preventing the patient from touching or manipulating the catheter. In addition, exemplary embodiments protect the insertion site from harm if the patient is moving the limb or extremity. In certain embodiments, the transparent cover can be opened or removed so the nurse can touch, or palpate, the skin around and at the insertion site, as is required in a complete assessment of the site. Exemplary embodiments allow such contact by the care provider and can minimize disruption to the patient by reducing the need to remove the entire device.

The device can also be removed when necessary (i.e. during supervised time to allow for safe movement of the extremity or when it is determined the catheter should be removed or replaced). Exemplary embodiments of the device can also act as a stabilizer for a catheter to substitute for over-taping or boarding of the extremity by including an optional removable stabilizing board to accompany or be used independent of the device.

Exemplary embodiments include a device for securing and monitoring a catheter, where the device comprises: a central portion comprising an aperture; a transparent panel extending across the aperture; a first elongated portion extending from a first side of the central portion; a second elongated portion extending from a second side of the central portion, where the second elongated portion is configured to couple to the first elongated portion; and a first support member coupled to the central portion and proximal to the aperture.

Certain embodiments further comprise a third elongated portion extending from the first side of the central portion; and a fourth elongated portion extending from the second side of the central portion, where the third elongated portion is configured to couple to the fourth elongated portion. Particular embodiments further comprise a second support member coupled to the central portion and proximal to the aperture, where the first support member is proximal to the first side of the central portion and the second support member is proximal to the second side of the central portion.

Some embodiments further comprise: a first coupling member configured to couple the first elongated portion and the second elongated portion; and a second coupling member configured to couple the third elongated portion and the fourth elongated portion. In specific embodiments, the first elongated portion comprises a plurality of notches configured to engage the first coupling member, such that the first coupling member can be coupled to the first elongated portion at a plurality of locations along a length of the first elongated portion; and the third elongated portion comprises a plurality of notches configured to engage the second coupling member, such that the second coupling member can be coupled to the third elongated portion at a plurality of locations along a length of the third elongated portion.

In certain embodiments, the first and second coupling members are configured as e-hooks. In particular embodiments the transparent panel is removable from the device, and in some embodiments the transparent panel comprises vents. In specific embodiments, the transparent panel is formed from an air-permeable material.

In certain embodiments, the central portion, the first elongated portion and the second elongated portion comprise a plurality of layers. In particular embodiments, the plurality of layers comprise: a first fabric layer; a first adhesive layer; a second fabric layer; a second adhesive layer; and a third fabric layer. In some embodiments the first and third fabric layers comprise an elastic fabric, and in specific embodiments the first and second adhesive layers comprise a thermoplastic adhesive film. In certain embodiments, the central portion comprises a foam layer, and in particular embodiments the foam layer comprises a polyurethane foam. In some embodiments the foam layer is between 0.125 inches thick and 0.5 inches thick, and in specific embodiments the foam layer is approximately 0.25 inches thick.

Exemplary embodiments include a method of securing and monitoring a catheter, where the method comprises: obtaining a device as disclosed herein (including for example, a device according to claim 1); placing the central portion of the device over an insertion site of the catheter such that aperture extends around the insertion site; wrapping the first elongated portion of the device around a first portion of an extremity of the patient; wrapping the second elongated portion of the device around a second portion of the extremity of the patient; coupling the first elongated portion of the device to the second elongated portion of the device; and monitoring the insertion site through the transparent cover extending over the aperture.

In certain embodiments, coupling the first elongated portion to the second elongated portion comprises engaging a first e-hook with the first and second elongated portions. Particular embodiments further comprise wrapping a third elongated portion of the device around a third portion of an extremity of the patient; wrapping a fourth elongated portion of the device around a fourth portion of the extremity of the patient; and coupling the third elongated portion of the device to the fourth elongated portion of the device. In particular embodiments, coupling the third elongated portion to the fourth elongated portion comprises engaging a second e-hook with the third and fourth elongated portions. Some embodiments further comprise removing the transparent panel from the device and palpating tissue around the insertion site.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Figure 1:
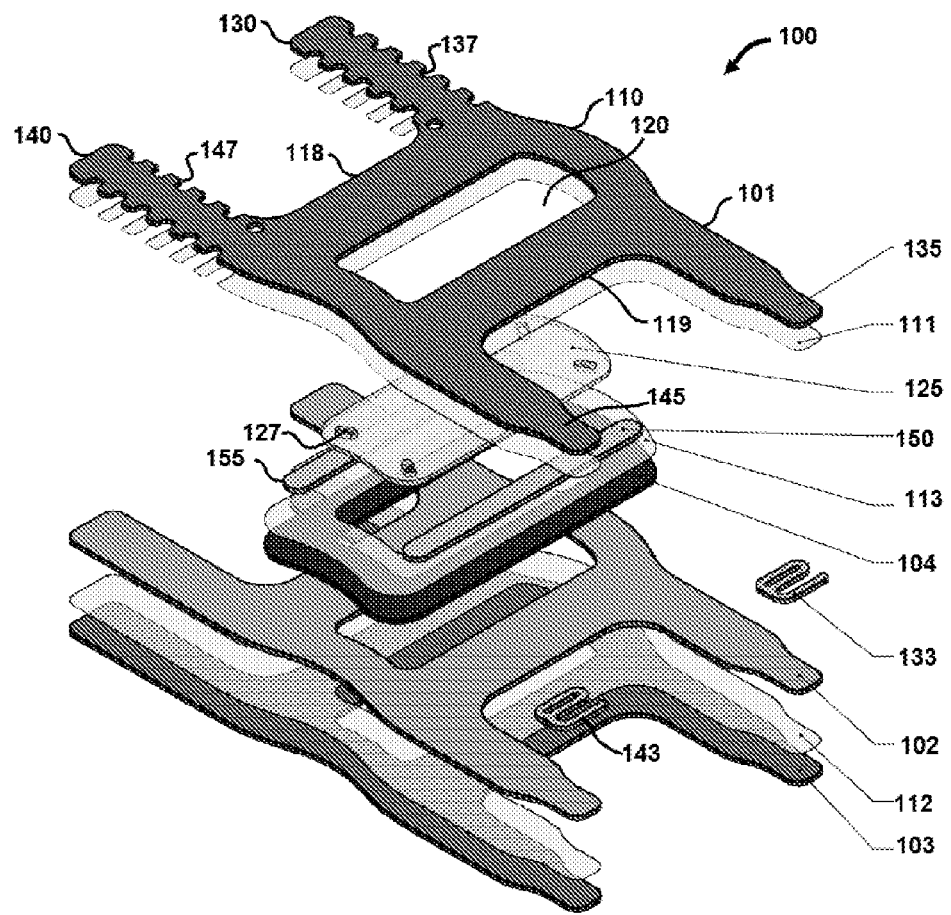
FIG. 1 illustrates an exploded perspective view of a device according to exemplary embodiments of the present disclosure.

Referring now to FIG. 1, exploded perspective and top views are shown of a device 100 for securing and monitoring an intravenous catheter. While particular features and components are shown and described in the exemplary embodiment shown in FIG. 1, it is understood that other exemplary embodiments of the present invention may comprise different features and components.

In this exemplary embodiment, device 100 comprises a central portion 110 comprising an aperture 120, with a transparent panel 125 extending across aperture 120. Device 100 also comprises a first support member 150 and a second support member 155 coupled to central portion 110 and proximal to aperture 120. Device 100 further comprises a first elongated portion 130 extending from a first side 118 of central portion 110, and a second elongated portion 135 extending from a second side 119 of central portion 110. In addition, device 100 also comprises a third elongated portion 140 extending from first side 118 and a fourth elongated portion 145 extending from second side 119. As shown in FIG. 1, central portion 110 and elongated portions 130, 135, 140 and 145 are configured such that device 100 generally forms a shape of the capital letter "H".

As explained in further detail below, first and second elongated portions 130, 135 are configured to couple together, and third and fourth elongated portions 140, 145 are also configured to couple together. For example, first and second elongated portions 130, 135 (as well as third and fourth elongated portions 140, 145) can be wrapped around a limb or other extremity to which device 100 is secured. This can allow for device 100 to be secured to a desired location on the patient such that central portion 110 and aperture 120 are located over an insertion site of a catheter, including for example, a peripheral intravenous (PIV) catheter.

In the embodiment shown in FIG. 1, device 100 also comprises a first coupling member 133 configured to couple first elongated portion 130 and second elongated portion 135. Device 100 further includes a second coupling member 143 configured to couple third elongated portion 140 and fourth elongated portion 145. In particular embodiments, first and second coupling members 133 and 143 can be configured as aluminum e-hooks (e.g. coupling members configured in the shape of a lower-case letter "e", as understood by those skilled in the art). It is understood that other embodiments may comprise different configurations for coupling elongated portions 130, 135, 140 and 145. For example, certain embodiments may comprise hook and loop arrangements, clips, hook and eye arrangements, snaps, buttons, zippers, ties, magnets, clasps, zip locks, or slide locks.

In specific embodiments, first and second elongated portions 130 and 140 comprise a plurality of notches 137 and 147 respectively. Notches 137 and 147 can be configured to engage first and second coupling member 133 and 143 such that first and second coupling members 133 and 143 can be coupled to first and second elongated portions 130 and 140 at a plurality of locations along the length of first and second elongated portions 130 and 140. Notches 137 and 147 also serve to help secure coupling members 133 and 143 to first and second elongated portions 130 and 140 and prevent accidental de-coupling with third and fourth elongated portions 135 and 145.

The ability to couple first and second coupling members 133 and 143 along different locations of first and second elongated portions 130 and 140 can allow device 100 to be secured to limbs or extremities of different sizes. Such a configuration can provide for increased comfort to the patient and improved securement of device 100 to the patient. In addition, device 100 can be manufactured in different size ranges to accommodate patients with different sized limbs or extremities. This can also provide for improved patient comfort and securement of device 100 to the patient.

In the embodiment shown in FIG. 1, device 100 (and in particular central portion 110 and first, second, third and fourth elongated portions, 130, 140, 135 and 145) comprises a plurality of layers of different materials. For example, device 100 may comprise a first fabric layer 101, a first adhesive layer 111, a second fabric layer 102, a second adhesive layer 112, and a third fabric layer 103. In addition, central portion 110 may comprise a foam layer 104, which can provide padding between first and second support members 150 and 155 and the patient and further increase comfort for the patient. Foam layer 104 can also accommodate irregularities in the surface surrounding the catheter insertion location to help secure the catheter, as explained further below. Particular embodiments may comprise a third adhesive layer 113 between foam layer 104 and support members 150 and 155 and transparent panel 125.

In specific embodiments, first fabric layer 101 and third fabric layer 103 may be an elastic or stretchable fabric (including for example Lycra® fabrics) and second fabric layer 102 may be a thicker fabric (including for example, a double knit fabric). Foam layer 104 may be configured from polyurethane foam in particular embodiments. Foam layer 104 may be between 0.125 inches thick and 0.5 inches thick in particular embodiments, including for example, a polyurethane foam layer approximately 0.25 inches thick. In certain embodiments, first, second, and third adhesive layers 111, 112 and 113 may be thermoplastic adhesive films (including for example Bemis® films) that bond adjacent layers together upon heating during the manufacturing process.

During use, device 100 can be placed over a catheter insertion site to secure the catheter and allow monitoring of the catheter insertion site while device 100 is in place. This can allow a care giver to verify the catheter has not withdrawn or been otherwise disturbed without removing device 100 and disturbing the patient. For example, central portion 110 can be located such that aperture 120 surrounds the insertion site and transparent panel 125 covers the insertion site.

With aperture 120 surrounding the insertion site, first and second elongated portions 130 and 135 can be wrapped around a patient's limb (or other extremity) and coupled together with first coupling member 133. Similarly, third and fourth elongated portions 140 and 145 can be wrapped around the limb or extremity and coupled together with second coupling member 143. Notches 137 and 147 can be used to adjust the locations along first and second elongated portions 130 and 140 where first and second coupling members 133 and 143 are engaged.

The ability to adjust the engagement location coupling members 133 and 143 can provide the desired amount of tension in elongated portions 130, 135, 140 and 145 around the extremity. This force can secure a catheter between the third fabric layer 103 and the patient's skin, while still maintaining comfort for the patient. In addition, the elastic nature of the materials used in portions of device 100 can also assist in securing a catheter without sacrificing patient comfort. Device 100 can therefore secure a catheter after insertion and reduce the likelihood of accidental withdrawal or dislodgement of the catheter or other unwanted movement of the catheter. This can increase patient comfort and safety and minimize the potential for unwanted complications.

In particular embodiments, transparent panel 125 may comprise holes or vents 127 to allow for ventilation of the insertion site and reduce condensation formation, which could impair visibility through transparent panel 125. In some embodiments, transparent panel 125 may be formed from an air-permeable material. Transparent panel 125 can also serve as a barrier to reduce the likelihood of external environmental conditions contaminating the insertion site.

In addition to catheter securement, device 100 also allows a care provider to assess and monitor the insertion site via transparent panel 125 without removing device 100. In particular embodiments, transparent panel 125 can be formed from a material that is sufficiently flexible to conform to the surface surrounding the insertion site, but also rigid enough to provide protection of the site from external forces. In certain embodiments, transparent panel 125 may be formed from a polymer material, including for example, polyvinyl chloride (PVC). In some embodiments, transparent panel 125 may be removable from device 110 so that a care provider can palpate the skin around and at the insertion site. This can allow the care provider to conduct a more thorough assessment of the site without needing to disturb the patient and remove device 110 from the patient's extremity.

In certain embodiments device 100 can be used in conjunction with a stabilization board. For example, a stabilization board can be place between device 100 and the patient's extremity before device 100 is coupled to the extremity with elongated portions 130, 135, 140 and 145. In such embodiments, the stabilization board may be placed on against the limb in an area that does not include the insertion site. In other embodiments, the stabilization board may include an aperture that surrounds the insertion site so that board can be placed between device 100 and the insertion site while still allowing monitoring of the insertion site. The stabilization board may also be used independent of device 100 in some embodiments.

In addition to the benefits noted above, device 100 also provides other advantages. For example, the adjustment of device 100 can be accomplished with minimal disturbing of the patient or others in the vicinity of the patient. Other typical adjustment mechanisms, such as hook-and-loop (e.g. Velcro®) fasteners can cause considerable noise when de-coupling components to provide adjustment. This can disturb the patient, or other patients in the same room, when components are de-coupled to perform adjustments.

Figure 2:
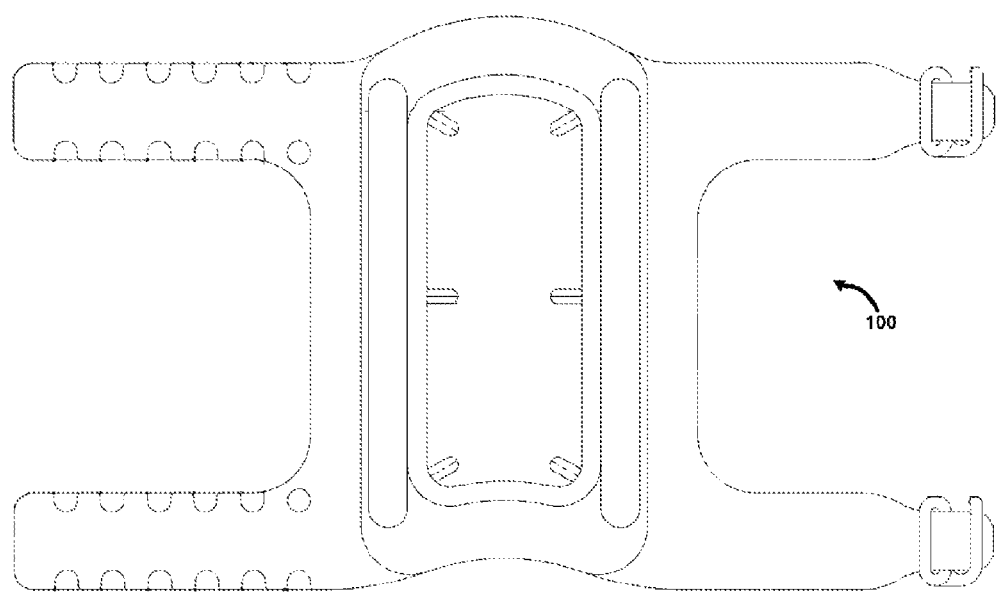
FIG. 2 illustrates a top view of the embodiment of FIG. 1.
Figure 3:
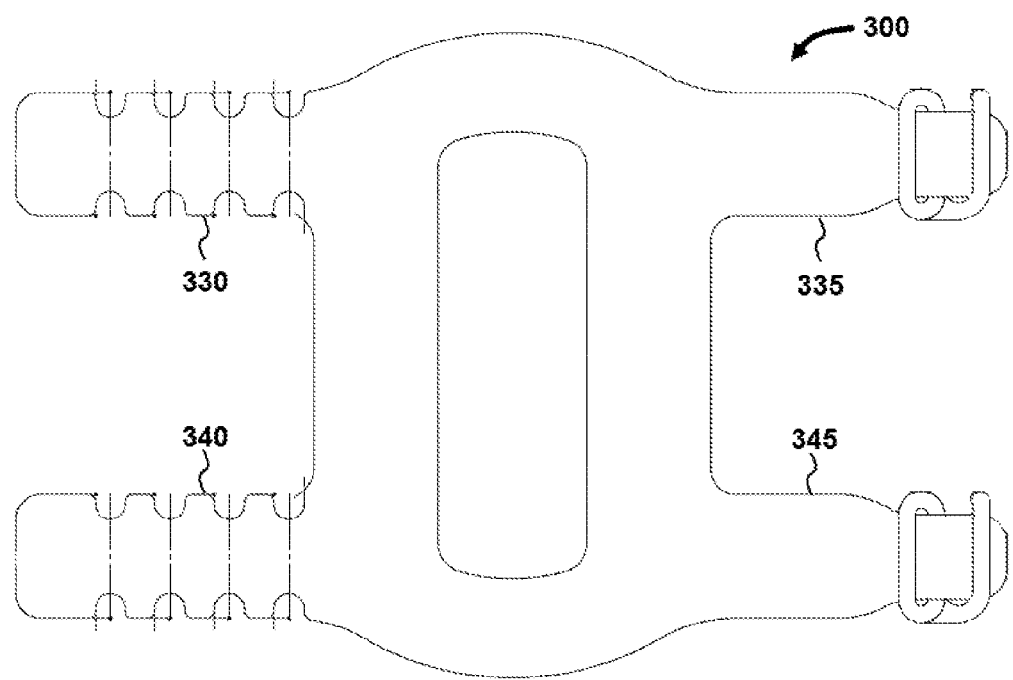
FIG. 3 illustrates a top view of a device according to exemplary embodiments of the present disclosure.

In addition to the embodiment shown in FIGS. 1 and 2, other exemplary embodiments of the present disclosure may include different sizes or configurations. For example referring now to FIG. 3, a device 300 is shown with features similar to device 100 but with smaller dimensions to accommodate smaller patient extremities. For sake of clarity, not all features of device 300 shown in FIG. 3 are labeled and described, but it is understood that features of device 300 function in a manner similar to that of device 100 shown in FIGS. 1 and 2. As shown in FIG. 3, elongated portions 330, 335, 340 and 345 are shorter in length than elongated portions 130, 135, 140 and 145 of device 100. This can allow device 300 to secure a catheter inserted in a smaller patient extremity in comparison to extremities accommodated by device 100.

Figure 4:
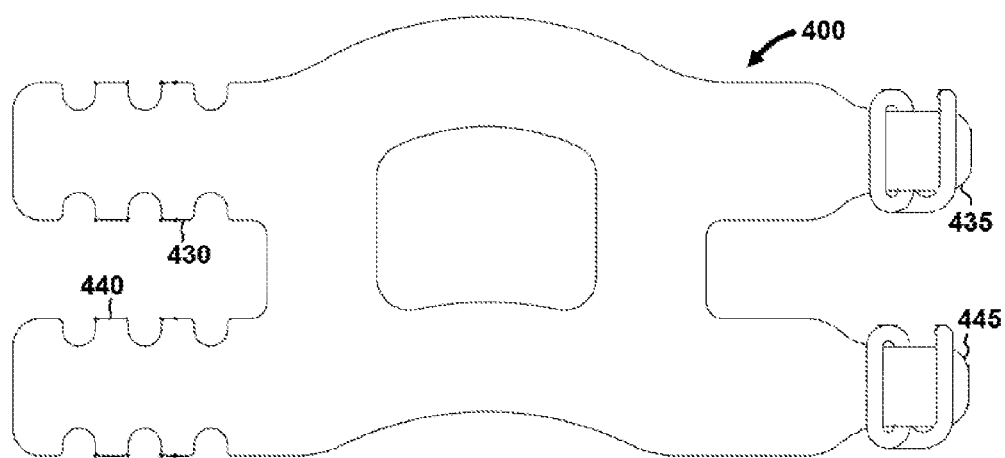
FIG. 4 illustrates a top view of a device according to exemplary embodiments of the present disclosure.

Referring now to FIG. 4, a device 400 is shown with features similar to devices 100 and 300, but with even smaller dimensions to accommodate smaller patient extremities. Again, for sake of clarity, not all features of device 400 shown in FIG. 4 are labeled and described, but it is understood that features of device 400 function in a manner similar to that of the previously described embodiments. As shown in FIG. 4, elongated portions 430, 435, 440 and 445 are shorter in length than elongated portions 330, 335, 340 and 345 of device 300. This can allow device 400 to secure a catheter inserted in a smaller patient extremity in comparison to extremities accommodated by device 300.

Accordingly, exemplary embodiments of the present disclosure provide significant benefits and advantages to both patients and care provides. Exemplary embodiments can effectively secure a catheter while still maintaining the ability to monitor the insertion site without removing the device. Exemplary embodiments also provide for ease of adjustment and comfort to the patient while minimizing the need to disturb the patient when monitoring the catheter insertions site. Furthermore, exemplary embodiments reduce the likelihood of unwanted complications including contamination of the insertion site.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:

1. Massa D J, Lundy J S, Faulconer A, Jr, Ridley R W (5 Jul. 1950). "A plastic needle.". Proc Staff Meet Mayo Clin 25 (14): 413-415.
2. Rivera A M, Strauss K W, Van Zundert A, Mortier E (2005). "The history of peripheral intravenous catheters: How little plastic tubes revolutionized medicine".
3. Soifer N E, Borzak S, Edlin B R, Weinstein R A (March 1998). "Prevention of peripheral venous catheter complications with an intravenous therapy team: a randomized controlled trial". Arch. Intern. Med. 158 (5): 473-7.
4. Griffith, Rebecca J; Jordan, Vanessa; Herd, David; Reed, Peter W; Dalziel, Stuart R (26 Apr. 2016). "Vapocoolants (cold spray) for pain treatment during intravenous cannulation". Cochrane Database of Systematic Reviews (John Wiley & Sons, Ltd).
5. CDC Morbidity and Mortality Weekly Report August 2002. "Guidelines for the Prevention of Intravascular Catheter-Related Infections"
6. Bregenzer T, Conen D, Sakmann P, Widmer A F (January 1998). "Is routine replacement of peripheral intravenous catheters necessary?". Arch. Intern. Med. 158 (2): 151-6.
7. Miller J M, Goetz A M, Squier C, Muder R R (1996).
8. U.S. Pat. No. 6,526,981
9. U.S. Pat. No. 5,897,519
10. U.S. Pat. No. 5,577,516
11. U.S. Pat. No. 5,456,660
12. U.S. Pat. No. 5,449,349
13. U.S. Pat. No. 5,336,195
14. U.S. Pat. No. 5,238,010
15. U.S. Pat. No. 5,167,240
16. U.S. Pat. No. 5,112,313
17. U.S. Pat. No. 5,074,847
18. U.S. Pat. No. 5,018,534
19. U.S. Pat. No. 4,930,500
20. U.S. Pat. No. 3,782,378
21. U.S. Pat. D335926
22. U.S. Pat. D359120

The invention claimed is:

1. A device for securing and monitoring a catheter, the device comprising:
a central portion comprising an aperture and a foam layer;
a transparent panel extending across the aperture, wherein the transparent panel comprises vents;
a first elongated portion extending from a first side of the central portion;
a second elongated portion extending from a second side of the central portion, wherein the second elongated portion is configured to couple to the first elongated portion;
a first support member coupled to the central portion and proximal to the aperture;
a second support member coupled to the central portion and proximal to the aperture, wherein:
the first support member is proximal to the first side of the central portion; and
the second support member is proximal to the second side of the central portion;
a third elongated portion extending from the first side of the central portion;
a fourth elongated portion extending from the second side of the central portion, wherein the third elongated portion is configured to couple to the fourth elongated portion;
the first elongated portion comprises a plurality of notches configured to engage the first coupling member, such that the first coupling member can be coupled to the first elongated portion at a plurality of locations along a length of the first elongated portion; and;
a first coupling member configured to couple the first elongated portion and the second elongated portion, wherein the first elongated portion comprises a plurality of notches configured to engage the first coupling member, such that the first coupling member can be coupled to the first elongated portion at a plurality of locations along a length of the first elongated portion; and
a second coupling member configured to couple the third elongated portion and the fourth elongated portion, wherein the third elongated portion comprises a plurality of notches configured to engage the second coupling member, such that the second coupling member can be coupled to the third elongated portion at a plurality of locations along a length of the third elongated portion, wherein:
the central portion, the first elongated portion and the second elongated portion comprise a plurality of layers;
the plurality of layers comprises:
a first fabric layer;
a first adhesive layer;
a second fabric layer;
a second adhesive layer; and
a third fabric layer;
the central portion comprises a foam layer configured to provide padding between the first and second support members and the second fabric layer;
the first and third fabric layers comprise an elastic fabric; and
the first and second adhesive layers comprise a thermoplastic adhesive film.

2. The device of claim 1 wherein the first and second coupling members are configured as e-hooks.

3. The device of claim 1 wherein the transparent panel is removable from the device.

4. The device of claim 1 wherein the vents are configured as holes in the transparent panel.

5. The device of claim 1 wherein the transparent panel is formed from an air-permeable material.

6. The device of claim 1 wherein the foam layer comprises a polyurethane foam.

7. The device of claim 1 wherein the foam layer is between 0.125 inches thick and 0.5 inches thick.

8. The device of claim 1 wherein the foam layer is 0.25 inches thick.

9. A method of securing and monitoring a catheter, the method comprising:
obtaining the device according to claim 1;
placing the central portion of the device over an insertion site of the catheter such that aperture extends around the insertion site;
wrapping the first elongated portion of the device around a first portion of an extremity of the patient;
wrapping the second elongated portion of the device around a second portion of the extremity of the patient;
coupling the first elongated portion of the device to the second elongated portion of the device; and
monitoring the insertion site through the transparent cover extending over the aperture.

10. The method of claim 9, wherein coupling the first elongated portion to the second elongated portion comprises engaging a first e-hook with the first and second elongated portions.

11. The method of claim 9 further comprising removing the transparent panel from the device and palpating tissue around the insertion site.

12. The method of claim 9 further comprising:
wrapping a third elongated portion of the device around a third portion of an extremity of the patient;
wrapping a fourth elongated portion of the device around a fourth portion of the extremity of the patient; and coupling the third elongated portion of the device to the fourth elongated portion of the device.

13. The method of claim 12 wherein coupling the third elongated portion to the fourth elongated portion comprises engaging a second e-hook with the third and fourth elongated portions.

\* \* \* \* \*